(12) United States Patent
Liu et al.

(10) Patent No.: US 11,097,086 B2
(45) Date of Patent: Aug. 24, 2021

(54) MICRO-NEEDLE SHEET FOR REDUCING WRINKLES

(71) Applicant: L'OREAL, Paris (FR)

(72) Inventors: Shu Liu, Kawasaki (JP); Kazuyuki Ohnishi, Osaka (JP)

(73) Assignee: L'OREAL, Paris (FR)

( * ) Notice: Subject to any disclaimer, the term of this patent is extended or adjusted under 35 U.S.C. 154(b) by 475 days.

(21) Appl. No.: 15/516,215

(22) PCT Filed: Nov. 13, 2015

(86) PCT No.: PCT/JP2015/082633
§ 371 (c)(1),
(2) Date: Mar. 31, 2017

(87) PCT Pub. No.: WO2016/076442
PCT Pub. Date: May 19, 2016

(65) Prior Publication Data
US 2017/0304602 A1    Oct. 26, 2017

(30) Foreign Application Priority Data

Nov. 14, 2014    (JP) .............................. JP2014-231306

(51) Int. Cl.
*A61M 37/00*    (2006.01)
*A61K 8/73*    (2006.01)
(Continued)

(52) U.S. Cl.
CPC ......... *A61M 37/0015* (2013.01); *A45D 44/22* (2013.01); *A61K 8/735* (2013.01);
(Continued)

(58) Field of Classification Search
CPC .... A45D 44/22; A61K 9/0021; A61K 9/0024; A61M 2037/0046; A61M 2037/0053; A61M 37/0015; A61M 2037/0061
See application file for complete search history.

(56) References Cited

U.S. PATENT DOCUMENTS 6,230,051 B1    5/2001    Cormier et al.
6,256,533 B1    7/2001    Yuzhakov et al.
(Continued)

FOREIGN PATENT DOCUMENTS

CN    101808588 A    8/2010
CN    103893018 A    7/2014
(Continued)

OTHER PUBLICATIONS

Japanese Office Action for counterpart Application No. 2014-231306, dated Jul. 9, 2018 with translation.
(Continued)

*Primary Examiner* — Deanna K Hall
(74) *Attorney, Agent, or Firm* — The Marbury Law Group, PLLC

(57) ABSTRACT

The present invention relates to a microneedle comprising a plurality of portions, wherein the plurality of portions comprise a distal end portion and a proximal end portion, at least two of the plurality of portions are made of different polymers, and the distal end portion is made of at least one polymer with high swellability and high viscoelasticity.

14 Claims, 4 Drawing Sheets

(51) Int. Cl.
  *A61K 8/81*    (2006.01)
  *A61Q 19/08*   (2006.01)
  *A61K 9/00*    (2006.01)
  *A61K 47/36*   (2006.01)
  *A61K 47/32*   (2006.01)
  *A61K 8/85*    (2006.01)
  *A45D 44/22*   (2006.01)
  *A61K 8/86*    (2006.01)
  *B29C 39/02*   (2006.01)
  *B29K 33/00*   (2006.01)
  *B29K 71/00*   (2006.01)
  *B29K 105/00*  (2006.01)
  *B29L 31/00*   (2006.01)

(52) U.S. Cl.
  CPC .............. *A61K 8/8164* (2013.01); *A61K 8/85* (2013.01); *A61K 8/86* (2013.01); *A61K 9/0021* (2013.01); *A61K 47/32* (2013.01); *A61K 47/36* (2013.01); *A61Q 19/08* (2013.01); *A61K 2800/805* (2013.01); *A61K 2800/91* (2013.01); *A61M 2037/0046* (2013.01); *A61M 2037/0053* (2013.01); *A61M 2205/0216* (2013.01); *A61M 2207/00* (2013.01); *B29C 39/026* (2013.01); *B29K 2033/00* (2013.01); *B29K 2071/02* (2013.01); *B29K 2105/0085* (2013.01); *B29L 2031/7544* (2013.01)

(56) References Cited

U.S. PATENT DOCUMENTS

| | | |
|---|---|---|
| 6,379,324 B1 | 4/2002 | Gartstein et al. |
| 6,451,240 B1 | 9/2002 | Sherman et al. |
| 6,565,532 B1 | 5/2003 | Yuzhakov et al. |
| 6,591,124 B2 | 7/2003 | Sherman et al. |
| 6,603,987 B2 | 8/2003 | Whitson |
| 6,611,707 B1 | 8/2003 | Prausnitz et al. |
| 6,652,478 B1 | 11/2003 | Gartstein et al. |
| 6,663,820 B2 | 12/2003 | Arias et al. |
| 6,743,211 B1 | 6/2004 | Prausnitz et al. |
| 6,749,792 B2 | 6/2004 | Olson |
| 6,767,341 B2 | 7/2004 | Cho |
| 6,821,281 B2 | 11/2004 | Sherman et al. |
| 6,908,453 B2 | 6/2005 | Fleming et al. |
| 6,924,087 B2 | 8/2005 | Yeshurun et al. |
| 6,931,277 B1 | 8/2005 | Yuzhakov et al. |
| 6,960,193 B2 | 11/2005 | Rosenberg |
| 7,027,478 B2 | 4/2006 | Ackley |
| 7,108,681 B2 | 9/2006 | Gartstein et al. |
| 9,549,746 B2* | 1/2017 | Woolfson |
| 2002/0082543 A1 | 6/2002 | Park et al. |
| 2006/0200069 A1 | 9/2006 | Cormier et al. |
| 2007/0134829 A1 | 6/2007 | Wilke et al. |
| 2008/0269685 A1 | 10/2008 | Parminder et al. |
| 2009/0182306 A1 | 7/2009 | Lee et al. |
| 2010/0256064 A1 | 10/2010 | Woolfson et al. |
| 2011/0028905 A1 | 2/2011 | Takada |
| 2014/0180201 A1* | 6/2014 | Ding ............... B29C 43/021 604/46 |
| 2014/0276378 A1 | 9/2014 | Chen et al. |

FOREIGN PATENT DOCUMENTS

| | | |
|---|---|---|
| CN | 104039382 A | 9/2014 |
| CN | 104069585 A | 10/2014 |
| CN | 104095761 A | 10/2014 |
| JP | 2010-540507 A | 12/2010 |
| JP | 2013-530785 A | 8/2013 |
| WO | 2004/002566 A1 | 1/2004 |
| WO | 2007/040938 A1 | 4/2007 |
| WO | 2009/040548 A1 | 4/2009 |
| WO | 2009/041627 A1 | 4/2009 |
| WO | 2014/004301 A1 | 1/2014 |
| WO | 2014/064632 A1 | 5/2014 |
| WO | 2014/150069 A1 | 9/2014 |

OTHER PUBLICATIONS

International Search Report for Application No. PCT/JP2015/082633, dated Mar. 2, 2016.
Korean Office Action for KR Application No. 10-2017-7010516, dated Oct. 9, 2019.
Chinese Office Action for counterpart Application No. 201580060625X, dated May 31, 2019 (with English Translation).
Translated Japanese Office Action for counterpart Application No. 2014-231306, dated May 25, 2020.
Partial Translation of Chinese Office Action for counterpart Application No. 201580060625.X, dated Aug. 10, 2020.

* cited by examiner

MICRO-NEEDLE SHEET FOR REDUCING WRINKLES

CROSS REFERENCE TO RELATED APPLICATIONS

This is a national stage application of PCT/JP2015/082633, filed internationally on Nov. 13, 2015, which claims priority to Japanese Application No. 2014-231306, filed on Nov. 14, 2014, both of which are incorporated by reference herein in their entireties.

TECHNICAL FIELD

The invention relates generally to delivery of a polymer with high swellability and high viscoelasticity using microneedles.

BACKGROUND ART

The Stratum Corneum (SC) constitutes the main barrier to exogenous substances, including small molecular weight material. Substances permeating the skin must diffuse through the highly organized intercellular lipid bilayers of the SC. This intercellular microroute, which is lipophilic, is the primary pathway for exogenous substances to pass through the SC barrier by passive diffusion along a concentration gradient between a delivery vehicle and the SC. The ideal property of a molecule capable of effective passive diffusion, and thus, penetration through the SC barrier is known to be a molecular mass less than 600 Da.

For high weight molecular molecules, techniques aimed at removing the SC barrier, such as tape-stripping and suction, laser, or thermal ablation are impractical, while needle-free injections have so far failed to replace conventional needle-based delivery.

The concept of using a microstructured device consisting of a plurality of microprotrusions to breach the stratum corneum barrier was first proposed in the 1970s. Various devices comprising solid microprotrusions have been developed to produce a system that will puncture the stratum corneum leaving microscopic holes and that will enable subsequent inward drug delivery or outward migration of interstitial fluid. The production of solid microprotrusions and microneedle arrays using for example silicon or polymers have been described in the art, for example see WO2009040548, U.S. Pat. Nos. 6,743,211, 6,743,211, 6,743,211, IE 2005/0825, U.S.60/749,086, U.S. Pat. Nos. 6,924,087, 6,743,211, 6,663,820, 6,743,211, 6,767,341, 6,743,211, 6,663,820, 6,652,478, 6,743,211, 6,749,792, 6,451,240, 6,767,341, 6,743,211, 6,230,051, 6,908,453, 7,108,681, 6,931,277B1, EP1517722B1, US20060200069A1, U.S. Pat. Nos. 6,611,707, 6,565,532, 6,960,193, 6,743,211, 6,379,324, WO2007/040938A1, U.S. Pat. Nos. 6,256,533, 6,743,211, 6,591,124, 7,027,478, 6,603,987, 6,821,281, and 6,565,532.

The use of such systems presently known in the art is associated with a problem of a very small amount of drug delivery.

Clearly, a robust alternative strategy is required to enhance high molecular weight transport across the SC.

DISCLOSURE OF INVENTION

As demonstrated, the present inventors have shown that microneedles according to the invention can puncture the stratum corneum with a high swellability and high viscoelasticity polymer.

Thus, in a first aspect of the present invention, there is provided a microneedle comprising a plurality of portions, wherein the plurality of portions comprise a distal end portion and a proximal end portion, at least two of the plurality of portions are made of different polymers, and the distal end portion is made of at least one polymer with high swellability and high viscoelasticity.

In one embodiment, at least one polymer with high swellability and high viscoelasticity has a high molecular weight between 500 kDa and 100000 kDa, preferably between 1000 kDa and 20000 kDa, and more preferably between 2100 kDa and 15000 kDa.

In one embodiment, the polymer with high swellability and high viscoelasticity is selected from the group consisting of hyaluronic acid, cross-linked hyaluronic acid, polyethylene glycol cross-linked PMVE/MA, a copolymer of methyl vinyl ether and a mixture thereof, and preferably the polymer with high swellability and high viscoelasticity is selected from the group consisting of cross-linked hyaluronic acid, polyethylene glycol cross-linked PMVE/MA, a copolymer of methyl vinyl ether and a mixture thereof. In one embodiment, the polymer with high swellability and high viscoelasticity is polyethylene glycol cross-linked PMVE/MA.

In one embodiment, the distal end portion contains a pore-forming carbonate agent. In one embodiment, at least the proximal end portion is water-dissolvable. In one embodiment, the distal end portion detaches following insertion into skin. In one embodiment, at least the proximal end portion degrades more rapidly than the distal end portion.

In one embodiment, the microneedle can puncture the stratum corneum of a mammal. In one embodiment, the distal end portion is an active ingredient. In one embodiment, the distal end portion comprises an active ingredient. In one embodiment, the distal end portion swells upon insertion into the skin. In one embodiment, the distal end portion swells upon insertion into the skin in less than 1 h. In one embodiment, the diameter of the distal end portion increases at least 2 times in one hour after insertion into the skin.

In a second aspect of the present invention, there is provided a sheet mask comprising a plurality of the microneedles.

In a third aspect of the present invention, there is provided a use of the microneedle in a cosmetic field and/or for reducing skin wrinkles.

In a fourth aspect of the present invention, there is provided a method of forming a sheet comprising an array of microneedles, comprising the steps of:
(a) providing a mold with cavities corresponding to a negative of the microneedles,
(b) filling a blend of materials comprising a polymer with high swellability and high viscoelasticity into the mold to mold a distal end portion,
(c) drying the mold,
(d) casting the mold with a blend of soluble materials,
(e) drying the mold, and
(f) unmolding the microneedles.

BEST MODE FOR CARRYING OUT THE INVENTION

A Microneedle for Use in Transport of a High Molecular Weight Polymer Across a Biological Barrier According to the invention, a polymer with high swellability is a polymer able to swell at least over 10 times in a 1-hour in vitro incubation in a physiological saline solution or phosphate buffered saline, preferably at least 20 times in 1-hour incubation, more preferably at least 30 times in 1-hour incubation, even more preferably at least 40 times in 1-hour incubation, and most preferably about 45-55 times in 1-hour incubation. This swelling ratio can be calculated by the method described in the example section below.

According to the invention, a polymer with high viscoelasticity is a polymer that will form a gel after the in vitro incubation in a physiological saline solution or phosphate buffered saline. The gel exhibits a high elastic modulus G', a high viscous modulus G", a Tangent ($\delta$) (Tangent ($\delta$)=G"/G') of less than 1, and a high consistency G* ($G^{*2}=G'^2+G''^2$) even at low frequency (0.01 Hz) in a dynamic frequency sweep test with a Rheometer.

In this application, reference is made to "microneedles" as the type of microprotrusion or microprojection which is being employed. It will be understood by persons of skill in the art that in many cases the same inventive principles apply to the use of other microprotrusions or microprojections to penetrate skin or other biological membranes. Other microprotrusions or microprojections may include, for example, microblades as described in U.S. Pat. No. 6,219,574 and Canadian Patent Application No. 2,226,718, and edged microneedles as described in U.S. Pat. No. 6,652,478. In general, it is preferred that the microprojections have a height of at least about 100 µm, at least about 150 µm, at least about 200 µm, at least about 250 µm, or at least about 300 µm. In general, it is also preferred that the microprojections have a height of no more than about 1 mm, no more than about 800 µm, no more than about 500 µm, or in some cases no more than about 300 µm. The microprojections may have an aspect ratio of at least 3:1 (height to diameter at base), at least about 2:1, or at least about 1:1.

In one embodiment, the microneedles are conical in shape with a circular base which tapers to a point at a height of the microneedle above the base. Suitably, in embodiments of the arrays of the invention, the microneedles can have a diameter of 1-500 µm at their base. In one embodiment, the microneedles of and for use in the invention can have a diameter in the range 50-300 µm, for example 100-200 µm. In another embodiment, the microneedles of the invention may be of a diameter in the range of 1 µm to 50 µm, for example in the range of 20-50 µm.

Proximal End Portion

Figure 9:
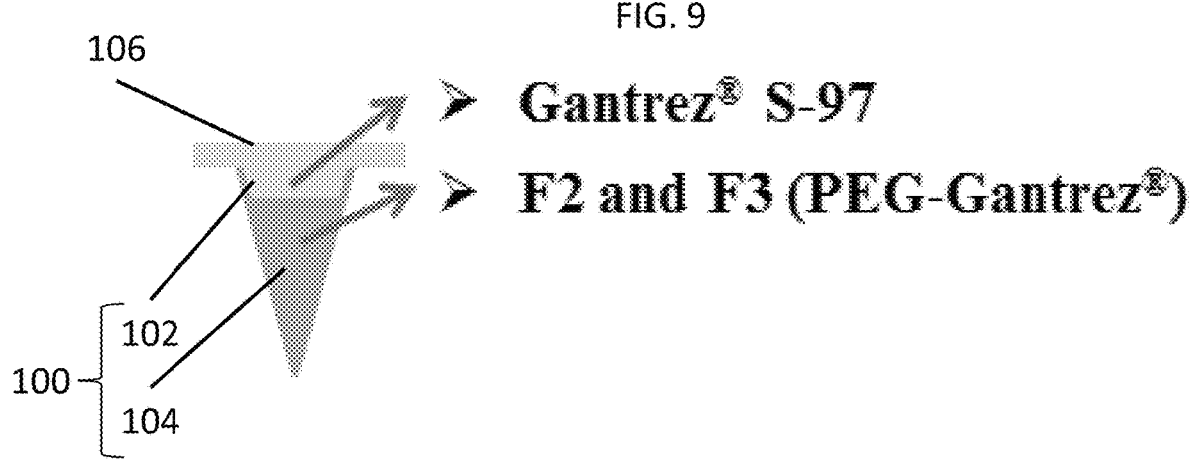
FIG. 9 is a schematic view of a microneedle according to various embodiments of the present disclosure.

As shown in FIG. 9, in one embodiment, a microneedle 100 may include a proximal end portion 102 disposed on a sheet 106, and a distal end portion 104 extending from the proximal end portion 102. The proximal end portion 102 is made of one or more soluble polymers. The proximal end portion 102 is a portion comprising proximal end. Examples of suitable polymers include, but are not necessarily limited to, hyaluronic acid with low molecular weight (preferably less than 50 KDa, more preferably less than 10 KDa); monosaccharide (for example, glucose, fructose, galactose); disaccharide (for example, sucrose, lactose, maltose); oligosaccharide, dextrin, dextran, polyethylene glycol, polyvinyl alcohol, poly (methyvinylether/maleic anhydride), polyvinylpyrrolidone, and Gantrez-type polymers.

In a particular embodiment of the invention, suitable polymers are Gantrez-type polymers such as poly(methyl/vinyl ether/maleic acid) (PMVE/MA) and esters thereof, and poly(methyl/vinyl ether/maleic anhydride) (PMVE/MAH).

Distal End Portion

As shown in FIG. 9, in one embodiment, the distal end portion 104 is made of one or more hydrogel-forming polymers. The distal end portion 104 is a portion comprising distal end. Examples of suitable polymers include, but are not necessarily limited to, hyaluronic acid with high molecular weight (preferably more than 500 kDa, more preferably more than 1000 kDa, even more preferably more than 2100 kDa); cross-linked hyaluronic acid; cross-linked polyethylene glycol; polyethylene glycol cross-linked poly-lactic acid/poly glycolic acid/poly-lactic-co-glycolic acid/poly dioxanone; poly(styrene)-block-poly(acrylic acid); polyethylene glycol cross-linked poly(methyl/vinyl ether/maleic acid) (PEG cross-linked PMVE/MA); cross-linked polyvinylpyrrolidone; sodium starch glycolate; cellulose; natural and synthetic gums; alginates; sodium polyacrylate; and PEG-crosslinked-Gantrez-type polymers (PEG cross-linked Gantrez).

Gantrez-type polymers include poly(methyl/vinyl ether/maleic acid) (PMVE/MA) and esters thereof, and poly (methyl/vinyl ether/maleic anhydride) (PMVE/MAH).

In a preferred embodiment of the invention, the polymer with high swellability and high viscoelasticity contains different percentages of a pore-forming agent, such as sodium carbonate ($Na_2CO_3$).

According to the invention, a pore-forming agent is an agent able to cause free acid groups on the polymer to ionise, thus repelling adjacent groups and opening up the structure even further.

In order to be used in transdermal delivery, microneedles must be capable of creating openings in the stratum corneum.

Suitably, the microneedles do not fracture with manual force when a pressure of insertion of less than 50.0 N $cm^2$, for example less than 20.0 N $cm^2$, such as less than 10 N $cm^2$ is exerted on microneedles along their length.

Release of the Distal End Portion

According to the invention, the proximal end portion is made of a polymer capable of being dissolved after insertion into the skin.

Thanks to the solubilization of the proximal end portion and the volume expansion of the distal end portion, the distal end portion will separate and remain in the skin.

Optional external water can be added to accelerate the dissolution of the proximal end portion combined with the application of a microneedle sheet which is applied before or after the microneedle sheet.

Drug Delivery

Optionally, crosslinking of polymers may be used to further vary the strength and swelling characteristics of microprotrusions as well as the release characteristics of the microprotrusions for delivery of an active agent. For example, a lightly-crosslinked hydrogel microprotrusion could rapidly deliver a drug where only one dose is required. A moderately-crosslinked hydrogel microprotrusion could be used to allow prolonged drug delivery, thus facilitating a constant drug delivery into the skin.

Use of Microneedle in a Sheet Mask

A microneedle can be any suitable size and shape for use in a sheet to puncture the stratum corneum. The microneedles of the sheet are designed to pierce and optionally cross the stratum corneum. Suitably, the height of the microneedles can be altered so as to allow penetration into the upper epidermis or as far as the deep epidermis.

The apical separation distance between each of the individual microneedles in a sheet can be modified to ensure penetration of the skin while having a sufficiently small separation distance to provide high transdermal transport rates. In embodiments of the device, the range of apical separation distances between microprotrusions can be in the range of 50-1000 μm, such as 100-400 μm, or 200-300 μm. This allows a compromise to be achieved between efficient penetration of the stratum corneum and enhanced delivery of the polymer with high swellability and high viscoelasticity.

It will be apparent to those skilled in the art that the microneedles of the invention can take any reasonable shape, including, but not limited to, cones, rods and/or pillars. As such, the microneedles may have the same diameter at the tip as at the base or may taper in diameter in the direction from the base to the tip.

Cosmetic Support for the Sheet

Supports are, for example, chosen from masks, wipes, patches, and in general all types of porous substrates. Preferably, these supports have an oblong structure, namely with a thickness smaller than the dimensions of the plane in which they are defined.

Another support may, for example, be a flocked applicator. This applicator comprises, for example, a body made of elastomer or of plastic, covered on its surface with a flocking.

The support may be cut so as to be in the form of a disc, a mask, a towel, a glove, a precut roll, or any other form suitable for a cosmetic use.

Use of Microneedles in the Cosmetic Field

The microneedle sheet is used to deliver a polymer with high swellability and high viscoelasticity to improve the aesthetic appearance of the skin, by reducing the appearance of wrinkles.

A reduction in the amount of matrix leads to a decrease in skin thickness and deterioration of skin elasticity, causing the formation of wrinkles.

The distal end portion located in the skin will further swell and increase volume along with its absorption of water in the skin. Such volume expansion beneath the skin surface of a wrinkle site pushes the wrinkles from inside the skin and makes the wrinkles become shallower and wider.

In a particular embodiment, the microneedles of the invention can be used to apply semi-permanent or permanent marking to the skin.

Method of Manufacturing Microneedle

Figure 10:
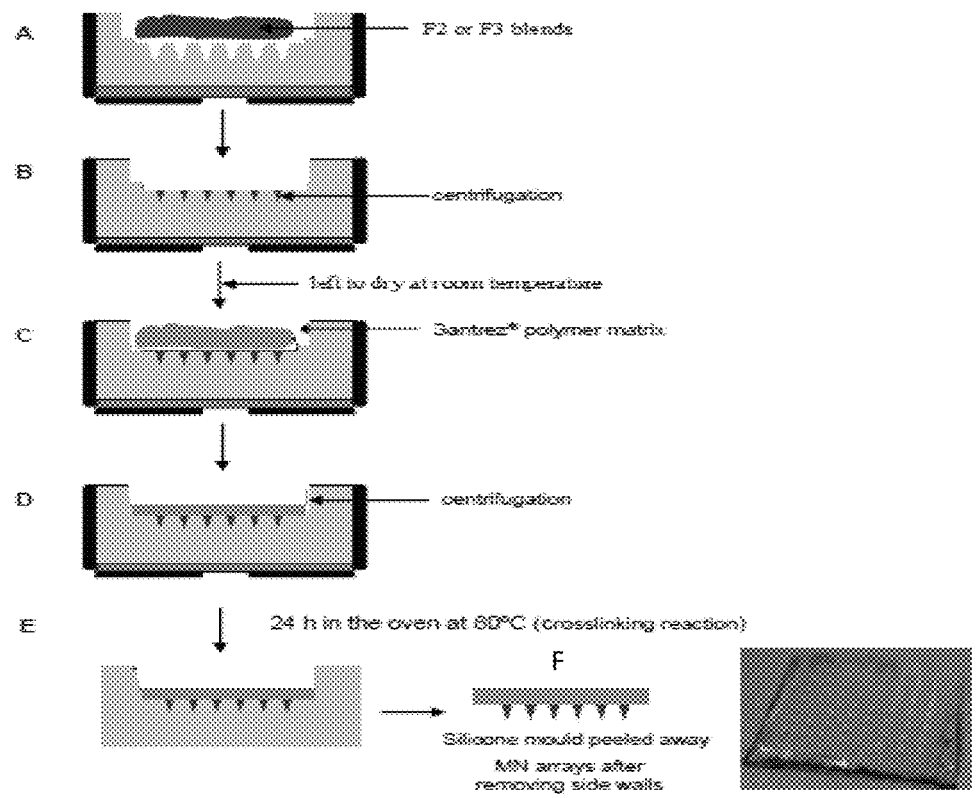
FIG. 10 is a schematic diagram showing a method of forming an array of microneedles.

FIG. 10 is a schematic diagram showing a method of forming an array of microneedles 100. Referring to FIGS. 9 and 10, the method comprises the steps of:

(a) providing a mold with cavities corresponding to a negative of the microneedles, (b) filling a blend of the materials with high swellability and high viscoelasticity into the casting mold to mold the distal end portion, (c) drying at room temperature for several hours, (d) casting the mold with a blend of the soluble materials, (e) drying at room temperature (and optionally heating), and (f) unmolding the microneedles and cutting the sheet 106 into desired shapes.

The invention will be better understood on reading the following descriptions, given solely by way of example, and with reference to the drawings.

EXAMPLES

The swellable materials of PEG cross-linked PMVE/MA, PEG cross-linked poly-lactic acid, hyaluronic acid, and cross-linked hyaluronic acid were screened in test 1 and test 2 to select the material for distal end portion of the microneedles from the point view of the swelling property and the viscoelasticity which is indicative of suitability for plumping and fixation in the skin. The swellable materials selected based on the results in the tests 1 and 2 were used in the prototyping of the microneedles. The insertion and the in-skin swelling of these prototypes over 48 hours were further investigated in test 3 and test 4.

Material Selection for Distal End Portion: In Vitro Swelling Property

Test Materials

PEG cross-linked PMVE/MA: Samples F1-4 were prepared by drying the aqueous polymeric blends (Table 1) for 48 hours at room temperature and curing at 80° C. in an oven for 24 hours to induce chemical crosslinking between PEG and PMVE/MA (Gantrez® S-97):

TABLE 1

| Formulation for PEG cross-linked PMVE/MA (PEG-PMVE/MA) | | | | |
|---|---|---|---|---|
| Sample (wt %) | PMVE/MA | PEG 10 kDa | $Na_2CO_3$ | Deionized water |
| F1 | 20 | 7.5 | 3 | 69.5 |
| F2 | 20 | 7.5 | 5 | 67.5 |
| F3 | 15 | 7.5 | 3 | 74.5 |
| F4 | 15 | 7.5 | 5 | 72.5 |

PEG cross-linked poly-lactic acid (PEG-PLAs)

TABLE 2

| PEG cross-linked poly-lactic acid (PEG-PLAs) for test | |
|---|---|
| EDL-40 | (DL) PEG-PLA, PEO 40 mol % |
| EDL-50 | (DL) PEG-PLA, PEO 50 mol % |
| EDL-60 | (DL) PEG-PLA, PEO 60 mol % |
| EL-40 | (L) PLA-co-PEG, PEO 40 mol % |

High Molecular Weight Hyaluronic Acid and Cross-Linked Hyaluronic Acid

TABLE 3

High molecular weight hyaluronic acid (HA) and cross-linked hyaluronic acid (HA)

| Cross-linked HA | Cross-linked hyaluronic acid |
|---|---|
| HA-1 | Hyaluronic acid, molecular weight of 1300-1800 kDa |
| HA-2 | Hyaluronic acid, molecular weight of 1800-2150 kDa |
| HA-3 | Hyaluronic acid, molecular weight of 2200 kDa |

Test Method:

The test materials were weighed as Wo and were swollen in a physiological saline solution over 7 hours at room temperature. At regular intervals, the materials were removed, wiped with filter paper to eliminate excess water and weighed as $W_t$. The swelling ratio was calculated using the following equation and then plotted into a graph.

$$\text{Swelling ratio at } t = \frac{W_t - W_0}{W_0}$$

Results

Figure 1:
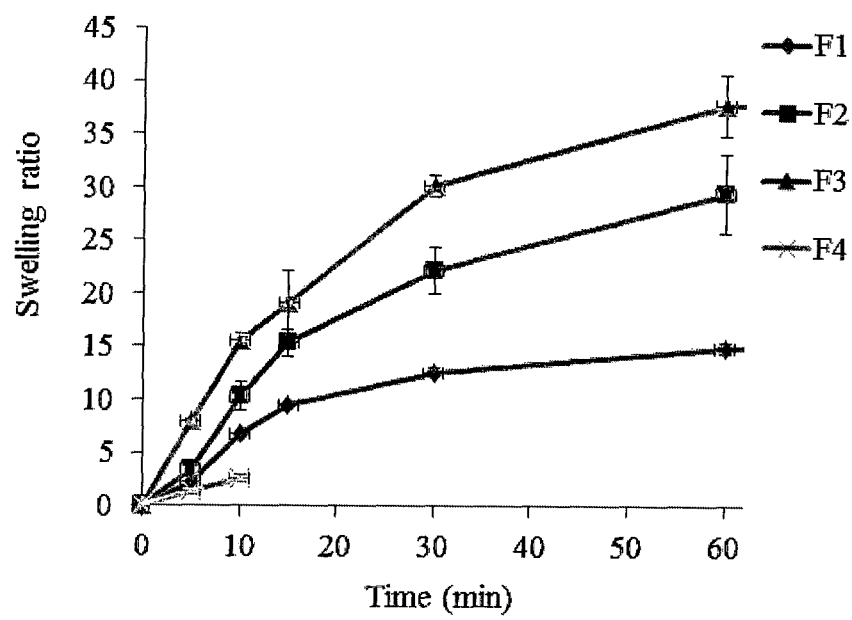
FIG. 1 shows swelling ratio of the PEG cross-linked PMVE/MA (F1~F4) prepared from the formulations specified in Table 2.

FIG. 1 shows the swelling ratio of the PEG cross-linked PMVE/MA (F1~F4). The swelling study of F4 was interrupted after 10 min because F4 was dissolving instead of swelling; however, the addition of $Na_2CO_3$ led to a significant increase in swelling. F2 and F3 had high fluid uptake capacity and also good mechanical strength when swollen.

Figure 2:
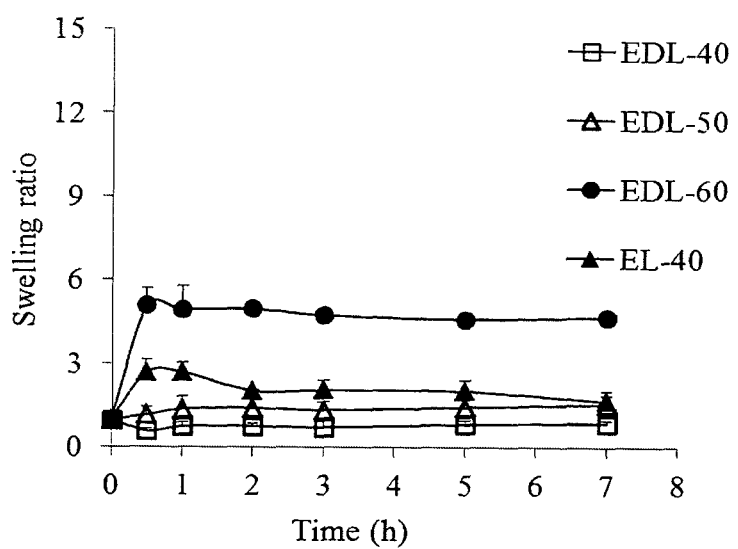
FIG. 2 shows swelling ratio of the PEG cross-linked PLAs specified in Table 2.

Swelling Property of PEG Cross-Linked PLAs:

FIG. 2 shows the swelling ratio of the PEG cross-linked PLAs specified in Table 2. The swelling properties of these materials was found to exhibit the following order: EDL-60>EL-40>EDL-50>EDL-40.

Figure 3:
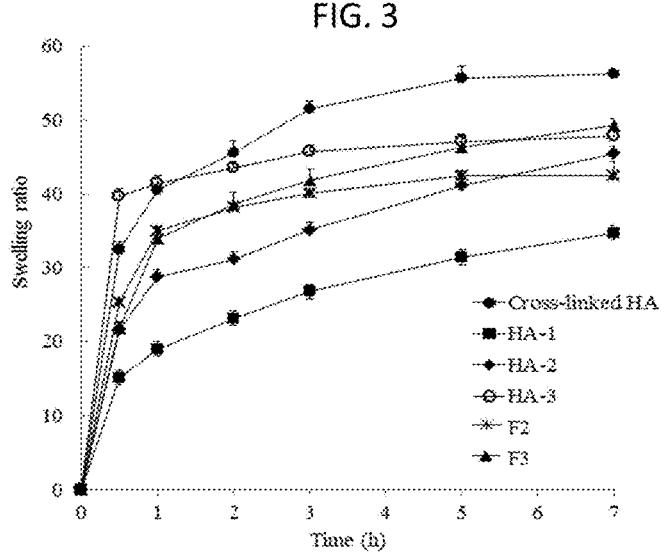
FIG. 3 shows swelling ratio of hyaluronic acids, cross-linked hyaluronic acid and PEG cross-linked PMVE/MA.

Swelling Property of High Molecular Weight HA, Cross-Linked HA and PEG Cross-Linked PMVE/MA (F2 and F3):

FIG. 3 compares the swelling property of hyaluronic acids (HA-1~3), cross-linked hyaluronic acid, and PEG cross-linked PMVE/MA (F2 and F3). High molecular weight HA showed better swelling over the 7 hour-incubation, and HA-3 showed the quickest swelling and highest swelling ratio among the three HAs with high molecular weight. The swelling properties of these materials was found to exhibit the following order: cross-linked HA>F3>HA-3>HA-2>F2>HA-1.

Conclusion:

The swelling property of selected materials was found to exhibit the following order: cross-linked HA>F3>HA-3>HA-2>F2>HA-1.

Material Selection for Distal End Portion: In Vitro Viscoelasticity

Test Materials

| Cross-linked HA | Cross-linked hyaluronic acid |
|---|---|
| HA-1 | Hyaluronic acid, molecular weight of 1300-1800 kDa |
| HA-2 | Hyaluronic acid, molecular weight of 1800-2150 kDa |
| HA-3 | Hyaluronic acid, molecular weight of 2200 kDa |
| F2 | prepared by drying the aqueous polymeric blend F2 in Table 2 for 48 h at room temperature and curing at 80° C. in an oven for 24 h to induce chemical crosslinking between PEG and PMVE/MA |
| F3 | prepared by drying the aqueous polymeric blend F3 in Table 2 for 48 h at room temperature and curing at 80° C. in an oven for 24 h to induce chemical crosslinking between PEG and PMVE/MA |

Test Method:

The test materials were put in strainers and incubated in a physiological saline solution at room temperature to mimic the swelling in skin. After 7 hours, the test materials swelled and formed gels in the strainers. These gels were removed and wiped with filter paper to eliminate excess water. The viscoelasticity was measured with a Rheometer in a dynamic frequency sweep test under the following conditions:

Geometry: Cone and Plate Geometry

Test Setup: Dynamic Frequency Sweep Test (Strain Control)

Strain: 0.1%

Temperature: 32° C.

Initial Frequency: 0.01 Hz

Final Frequency: 10 Hz

Points Per decade: 10

The tan (δ) and G* were calculated using following equation and then plotted into a graph.

$$\text{Tan}(\delta) = \frac{G'' \text{ loss modulus}}{G' \text{ storage modulus}}, G^{*2} = G'^2 + G''^2$$

Figure 4:
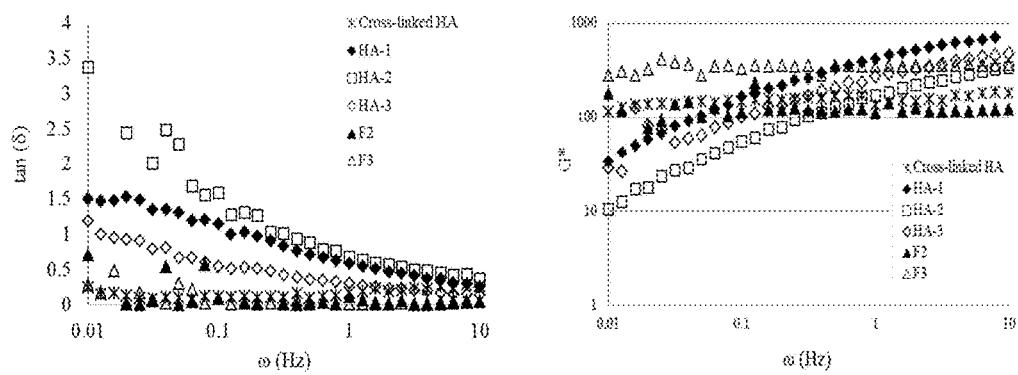
FIG. 4 shows viscoelasticity of the gels in dynamic frequency sweep test.

Results:

FIG. 4 shows the viscoelasticity of the gels measured with Rheometer. Tan (δ) with a value lower than 1 means more elastic behavior than viscous character, in which the material behaves more like a gel. This physicochemical behavior is indicative of suitability for plumping and fixation in the skin, especially in the case of low frequency 0.01-0.1 Hz that mostly mimics the contact with skin. Therefore, according to the value of tan (δ), the gel behavior of the materials for fixation exhibited the following order: cross-linked HA, F3, F2, HA-3, HA-1 and HA-2. A higher G* means higher firmness of the gels, which indicates the potential to resist compression by skin to maintain the shape. According to the value of G* especially at low frequency, the firmness of the materials is exhibited the following order: F3, cross-linked HA, F2, HA-1, HA-3 and HA-2.

Conclusion

Most of the materials evaluated have a low tan (δ) and a high G*, which is good for shape maintaining and fixation in skin. The three best materials were found to be F3, cross-linked HA, and F2. Since the swelling property exhibited the order of cross-linked HA>F3>HA-3>HA-2>F2>HA-1, the swelling property and viscoelasticity need to be balanced to select the materials for the distal end portion of the microneedle. F2, F3, and the cross-linked HA were found to be the best for the distal end portion of the microneedles.

In-Skin Insertion of the Microneedles (MN) with PEG Cross-Linked PMVE/MA (F2/F3) as the Distal End Portion Test samples: FIG. 9 is a representative illustration of the test sample MNs described below.

| Sample | Needle length | Distal end portion | Proximal end portion | |
|---|---|---|---|---|
| MN-1-F2 | 420 μm | F2 in table 2 | PMVE/MA | (Gantrez ® S-97) |
| MN-1-F3 | 420 μm | F3 in table 2 | PMVE/MA | (Gantrez ® S-97) |
| MN-2-F2 | 280 μm | F2 in table 2 | PMVE/MA | (Gantrez ® S-97) |
| MN-2-F3 | 280 μm | F3 in table 2 | PMVE/MA | (Gantrez ® S-97) |

Test Method:
Preparation of the Microneedles:

The microneedles (MN) were prepared in a two-step process according to the diagrammatic representation shown in FIG. 10, using the molds of MN-1 with a height of 420 μm and the molds of MN-2 with a height of 280 μm:

0.05 g of the F2 or F3 blend (Table 2) was put into the molds and the blend was spread with a spatula to cover the entire area of the MN holes.

The MN molds were centrifuged to force the blend into the MN holes.

The MNs were left to dry at room temperature.

Then, PMVE/MA (Gantrez® S-97) was cast into the molds.

The MN molds were centrifuged to force the blend into the MN holes.

The MNs were then left to dry and put into the oven at 80° C. for 24 h.

Then, the MNs were removed from the molds and the side walls were cut with a warm scalpel.

Ex Vivo Penetration of MN into the Skin

Full-thickness excised porcine skin was set onto a bed of tissue wetted with phosphate buffered saline to simulate the underflow of interstitial fluid. The skin was tensed and fixed with metal pins onto a support to simulate an in vivo situation. The MN samples were manually inserted with a thumb for 30 seconds into full-thickness neonatal pig skin applying a force similar that the used when pressing a button to call an elevator. Transparent adhesive tape was used to keep the MNs in place. Optical coherence tomography (OCT) was used to assess the penetration depth of the MNs into the skin.

Results

Figure 5:
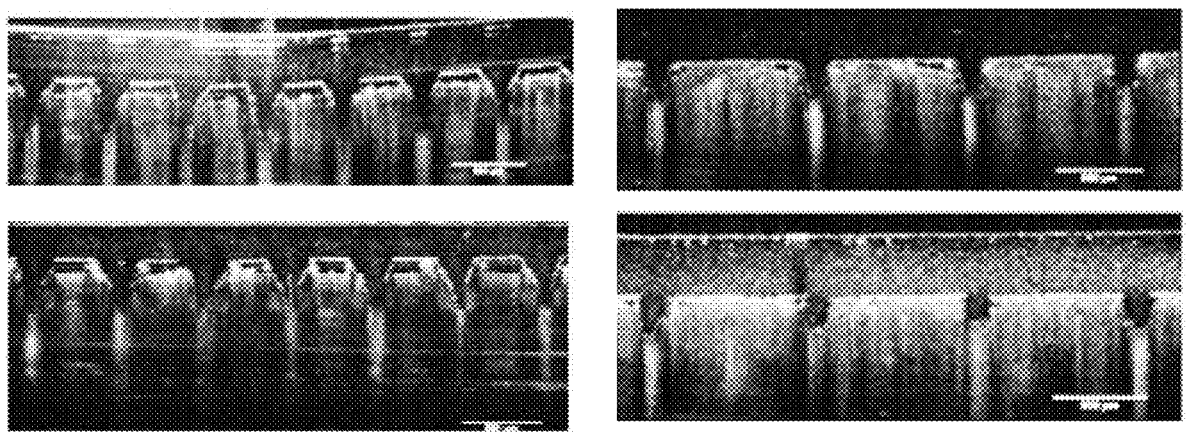
FIG. 5 shows OCT images after insertion of MN-1 (420 µm) prepared from F2 (A) and F3 (B) formulations and MN-2 (280 µm) prepared from F2 (C) and F3 (D) inserted across full-thickness neonatal porcine skin by applying pressure for 30 s.

FIG. 5 shows the penetration depth of the MNs (MN-1-F2/F3 and MN-2-F2/F3) across full-thickness neonatal porcine skin, and Table 4 shows the average insertion depth of the different MNs. The observed penetration variability can be explained by the different penetration rate observed from the different MNs of the same MN array. All the needles made of F2 and F3 successfully penetrated into skin as indicated in the OCT images below (FIG. 4). Approximately 74% of the length of MN-1-F2/F3 (~310 μm) and 72% of the length of MN-2-F2/F3 (~200 μm) penetrated into the skin.

TABLE 4

Average of the penetration depth the different MN arrays (Mean ± S.D., n = 4).

| Test sample | Insertion depth (μm) | Penetrated skin layer |
|---|---|---|
| MN-1-F2 | 313 ± 13 | Dermis |
| MN-1-F3 | 309 ± 4 | Dermis |
| MN-2-F2 | 198 ± 16 | Epidermis |
| MN-2-F3 | 207 ± 9 | Epidermis |

Conclusion

Two prototypes were successfully prepared using F2 and F3 materials as the distal end portion with the soluble Gantrez as the proximal end portion. Both prototypes penetrated into the skin without breakage as shown in the OCT images with an average of 72-74% of their total length.

In-Skin Swelling of the Microneedles (MN) with PEG-PMVE/MA (F2/F3) as the Distal End Portion Test Samples:

| Sample | Needle length | Distal end portion | Proximal end portion |
|---|---|---|---|
| MN-F2 | 600 μm | F2 in table 2 | PMVE/MA (Gantrez ® S-97) |
| MN-F3 | 600 μm | F3 in table 2 | PMVE/MA (Gantrez ® S-97) |

The microneedles were prepared in a two-step process following the procedure detailed in Test 3 on page 8 using the molds of MN with a height of 600 μm.

Test Method:
Swelling of MNs into the Skin

Full-thickness excised pig skin was set onto a gel wound dressing, and pre-equilibrated in phosphate buffered saline for 24 hours in order to simulate the underflow of interstitial fluid. The skin was tensed and fixed with metal pins on a support to simulate an in vivo situation. The MNs were manually inserted into the skin. The set up was kept in an incubator at 37° C. during the experiment. OCT was used to monitor the swelling of the MNs into the skin, and the variation of MN volume was studied at set times: 0, 0.5, 1, 3, 6, 24 and 48 h.

Results

Figure 6:
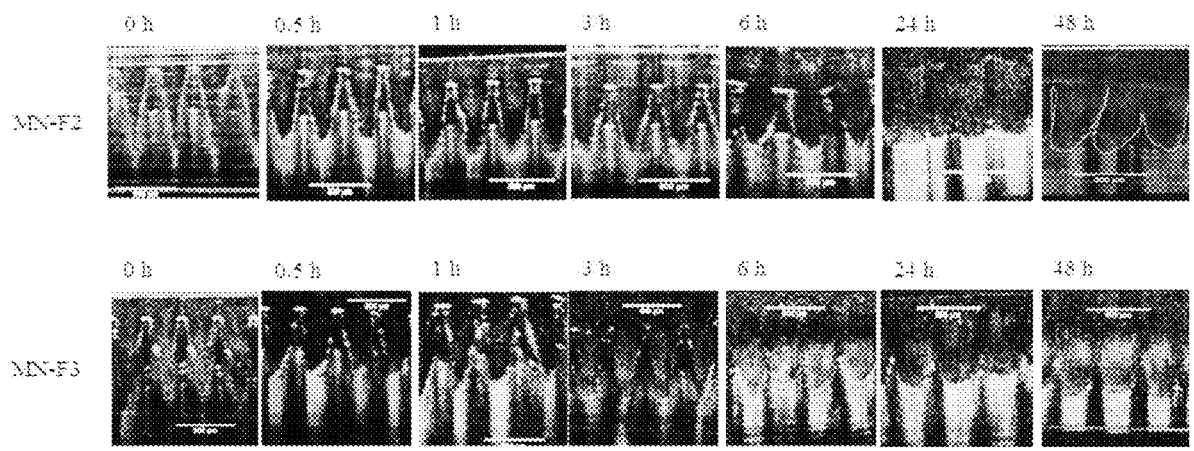
FIG. 6 shows OCT images of MN-F2 and MN-F3 swelling over 48 h into full-thickness porcine skin.

MN-F2 and MN-F3 were prototyped in line with their dimensions using the molds of MN with a height of 600 μm. FIG. 6 shows that MN-F2 and MN-F3 exhibited a change in shape and swelled in the skin at different time intervals. The distal end portion of MN-F2 and MN-F3 was observed to keep plumping the skin and staying in the skin at least for 48 hours.

Figure 7:
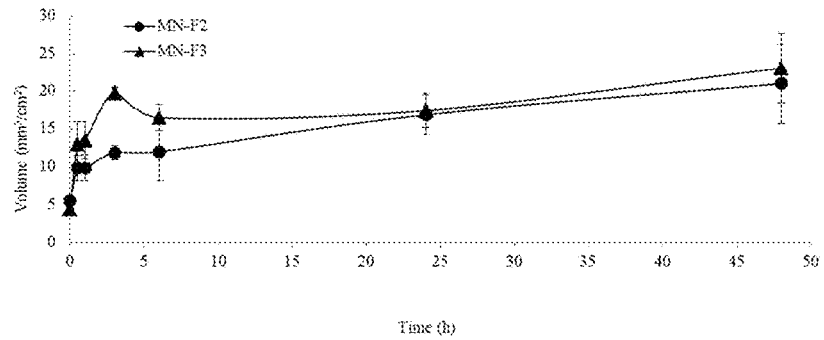
FIG. 7 shows volume (in $mm^3/cm^2$) of the MNs at different time intervals (Mean±SD, n=5).

FIG. 7 plotted the volume taken up by the MNs per $cm^2$ over 48 hour-insertion in skin. The calculations were carried out using the average volume of a single MN at the different time points; the MN arrays cover a surface of 0.5×0.5 cm, in which there are 361 MN. After 48 hours of insertion in the skin, the volume of fluid taken up by MN-F2 and MN-F3 on a surface measuring 1 $cm^2$ was 21.02±5.29 and 23.08±4.65 μl/$cm^2$, respectively. As shown in FIG. 7, the overall volume taken up by MN-F3 was found to be greater at the different time points in comparison to MN-F2, indicating the swelling of the distal end portion of both MNs begins immediately after the insertion into skin and lasts for at least 48 hours.

Figure 8:
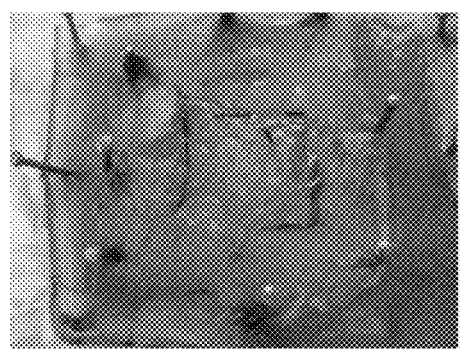
FIG. 8 shows swollen MNs left inserted in the full-thickness porcine skin after the removal of the transparent adhesive tape.

After the application, the distal end portions of MN-F2 and MN-F3 were left inserted in the skin due to the dissolution of the soluble proximal end portion as shown in FIG. 8.

Conclusion

MN-F2 and MN-F3 were prototyped in line with their dimensions using F2 and F3 as the distal end portion. The distal end portion of the two MNs was successfully left in the skin after the application. The swelling of the distal end portion of the two MNs was well observed during the 48 hour-insertion in the skin, and MN-F3 showed better swelling (about 5 times swelling) than MN-F2. Their plumping and fixation in the skin were observed to last for at least 48 hours.

The invention claimed is:

1. A method of cosmetic treatment of skin with at least one microneedle, comprising inserting the at least one microneedle into the skin, the at least one microneedle comprising:
- a proximal end portion; and
- a distal end portion extending from the proximal end portion and configured to penetrate the stratum corneum of the skin, wherein:
- the proximal end portion is configured to dissolve more rapidly in water than the distal end portion;
- the proximal end portion comprises at least a first polymer that is water-dissolvable and selected from the group consisting of hyaluronic acid with a molecular weight of less than 50 kDa, disaccharide, oligosaccharide, dextrin, dextran, polyethyleneglycol, polyvinyl alcohol, polyvinylpyrrolidone, poly(methylvinylether/maleic acid) (PMVE/MA), poly(methylvinylether/maleic anhydride) (PMVE/MAH), or mixtures thereof;
- the distal end portion is configured to detach from the proximal end portion following insertion into skin;
- the distal end portion comprises at least one second polymer, different from the first polymer, wherein the second polymer is selected from the group consisting of hyaluronic acid with a molecular weight of about 500 kDa or more, cross-linked hyaluronic acid, polyethylene glycol cross-linked poly-lactic acid, polyethylene glycol cross-linked PVME/MA, or mixtures thereof, and wherein the cosmetic treatment comprises reducing wrinkles on the skin.

2. The method of cosmetic treatment of the skin according to claim 1, wherein the at least one second polymer in the distal end portion is selected from the group consisting of hyaluronic acid with a molecular weight of about 500 kDa or more, cross-linked hyaluronic acid, polyethylene glycol cross-linked PMVE/MA, or mixtures thereof.

3. The method according to claim 1, wherein the at least one second polymer in the distal end portion has a molecular weight ranging from about 500 kDa to about 100000 kDa.

4. The method according to claim 1, wherein the at least one second polymer in the distal end portion has a molecular weight ranging from about 2100 kDa to about 15000 kDa.

5. The method according to claim 1, wherein the at least one second polymer in the distal end portion comprises polyethylene glycol cross-linked PMVE/MA.

6. The method according to claim 1, wherein the distal end portion comprises a pore-forming carbonate agent.

7. The method according to claim 1, wherein the proximal end portion is conical and the distal end portion tapers to a point.

8. The method according to claim 1, wherein the distal end portion and the proximal end portion each have a diameter ranging from about 50 μm to about 300 μm.

9. The method according to claim 1, wherein the distal end portion is formed of at least one active ingredient.

10. The method according to claim 1, wherein the distal end portion comprises at least one active ingredient.

11. The method according to claim 1, wherein the distal end portion is configured to swell upon insertion into the skin.

12. The method according to claim 1, wherein the diameter of the distal end portion increases by at least 100% over a time period of one hour after insertion into the skin.

13. A method of forming a sheet comprising a plurality of microneedles, the method comprising:
- filling a mold with a first material;
- drying the first material to form distal end portions of the microneedles;
- filling the mold with a second material; and
- drying the second material to form proximal end portions of the microneedles that extend from respective ones of the distal end portions, wherein the second material is more water soluble than the first material; and wherein:
- the distal end portions are configured to detach from the proximal end portion following insertion into skin;
- the first material comprises at least one polymer selected from the group consisting of hyaluronic acid with a molecular weight of about 500 kDa or more, cross-linked hyaluronic acid, polyethylene glycol cross-linked poly-lactic acid, polyethylene glycol cross-linked poly(methyl/vinyl ether/maleic acid) (PMVE/MA), or mixtures thereof; and
- the second material comprises at least one water-dissolvable polymer selected from the group consisting of hyaluronic acid with a molecular weight of less than 50 kDa, disaccharide, oligosaccharide, dextrin, dextran, polyethyleneglycol, polyvinyl alcohol, polyvinylpyrrolidone, PMVE/MA, poly(methylvinylether/maleic anhydride) (PVME/MAH), or mixtures thereof.

14. The method of forming a sheet according to claim 13, wherein the first material comprises hyaluronic acid with a molecular weight of about 500 kDa or more, cross-linked hyaluronic acid, polyethylene glycol cross-linked PMVE/MA, or mixtures thereof.

* * * * *